US00PP09157P

United States Patent [19]

Enthoven

[11] Patent Number: Plant 9,157

[45] Date of Patent: Jun. 6, 1995

[54] GERANIUM PLANT NAMED "MERIHONEY"

[75] Inventor: Adrianus W. M. Enthoven, Wateringen, Netherlands

[73] Assignee: Enthoven Breeding B.V., Wateringen, Netherlands

[21] Appl. No.: 217,124

[22] Filed: Mar. 24, 1994

[51] Int. Cl.[6] ..... A01H 5/00
[52] U.S. Cl. ..... Plt./87.12
[58] Field of Search ..... Plt. 87.12

[56] References Cited

U.S. PATENT DOCUMENTS

P.P. 8,669 3/1994 Trees ..... Plt./87.12

*Primary Examiner*—James R. Feyrer
*Attorney, Agent, or Firm*—Foley & Lardner

[57] ABSTRACT

A new and distinct cultivar of geranium named Merihoney, particularly characterized by the combined features of single red flowers, asymmetric flower buds, large inflorescence with many open flowers; relatively long and dark red pedicels; compact plant growth habit; dark green foliage with a light zone on the upper side; leaf margins that are double crenated and slightly incised; flowering is early and uniform and the flowers are strongly rain resistant.

3 Drawing Sheets

The present invention comprises a new and distinct cultivar of geranium, botanically known as *Pelargonium zonale,* and hereinafter referred to by the cultivar name Merihoney.

Merihoney is a product of planned breeding program which had the objective of creating new geranium cultivars with semi-double flower form, compact habit, fast rooting, good tolerance to botrytis, superior weather resistance and little need for growth regulators.

Merihoney was originated from a hybridization made by the inventor in a controlled breeding program in Wateringen, The Netherlands in 1986.

The female parent was a proprietary Enthoven seedling Nr. 13, characterized by it compact growth. The male parent of Merihoney was a proprietary Enthoven seedling Nr. 7.03, characterized by its weather resistance.

Merihoney was discovered and selected as one flowering plant within the progeny of the stated cross by Adrianus W. M. Enthoven in June 1987 in a controlled environment in Wateringen, The Netherlands.

The first act of asexual reproduction of Merihoney was accomplished when vegetative cuttings were taken from the initial selection in August 1987 in a controlled environment in Wateringen, The Netherlands under the supervision of Andrianus W. M. Enthoven.

Horticultural examination of selected units initiated in Spring and Summer 1988 and continuing thereafter has demonstrated that the combination of characteristics as herein disclosed for Merihoney are firmly fixed and retained through successive generations of asexual reproduction.

Merihoney has not been observed under all possible environmental conditions. The phenotype may vary with variations in environment such as temperature, light intensity and day length, without, however, any variation in genotype.

The following measurements, and comparison describe plants grown in Wateringen, The Netherlands under greenhouse and outdoors conditions which approximate those generally used in commercial practice.

The following traits have been repeatedly observed and are determined to be basic characteristics of Merihoney, which in combination distinguish this geranium as a new and distinct cultivar:

1. The plant has a compact growth habit.
2. The foliage is dark green with a light zone on the upperside (RHS 137A).
3. The leaf margins are double crenated and slightly incised.
4. The leaf stalk is short.
5. The peduncle is thick and short to medium in height extending the flowers well above the foliage.
6. The inflorescence is large with many open flowers.
7. The flower pedicels are rather long with a dark red color.
8. The flower buds are asymmetric in shape.
9. The flowers have a large diameter, are single and the color is red.
10. The buds are able to develop with rather low light, so that the plant flowers early.
11. The plants are strongly rain resistant.
12. Due to dark green foliage the plants are better able to endure lengthy transportation.
13. The plant has a consistent uniform growth habit as a result of which plants of Merihoney generally flower at the same time.

Of the many commercial cultivars known to the present inventor, the most similar in comparison to Merihoney is the cultivar Osna. Reference is made to attached Chart A which compares certain characteristics of Merihoney to those same characteristics of Osna.

In general comparison to Osna, Merihoney has, among other things, a very weak to weak zone area on the upper side of the leaf blade, and a smaller diameter of inflorescence.

The accompanying color photographic drawings show typical flower and foliage characteristics of Merihoney, with colors being as true as possible with illustrations of this type. Scales in centimeters appear in each photo to better show dimension.

The photo on Sheet 1 is a side view of Merihoney grown in a 10.5 cm pot approximately 8 weeks, showing the foliage, flower stalks and inflorescences.

The photo on Sheet 2 is a close-up view of the upper and lower sides of typical leaves of Merihoney and The photo on Sheet 3 is a close-up view showing the top and bottom surfaces of typical flowers of Merihoney.

In the following description color references are made to the Royal Horticultural Society Colour Chart (RHS) and Horicultural Colour Chart (HCC). The color values were determined between 2:45 and 3:00 p.m. on Jul. 15, 1988 under 22,300 Klux light intensity at Wateringen, The Netherlands.

Classification:

*Botanical.*—A hybrid of the genus *Pelargonium zonale* cv. Merihoney.

*Commercial.*—Zonal geranium.

INFLORESCENCE

A. Umbel:

*Average diameter.*—Indoor: 132 mm.

*Average depth.*—Indoor: 95 mm.

*Peduncle length.*—Indoor: 152 mm.

*Pedicel length.*—Indoor: 37 mm.

*Pedicel color.*—Dark red.

Corolla:

*Average diameter.*—Indoor: 47 mm.

*Form.*—Single (5 petals).

*Color (general tonality of a distance of three meters).*—RHS 40A, HCC 717.

*Color (main body, upper surface).*—RHS 40A, HCC 717.

*Color (near margin upper face).*—RHS 40A, HCC 717.

*Diameter lower petals.*—20 mm.

*Length lower petals.*—25 mm.

*Diameter upper petals.*—17 mm.

*Length upper petals.*—26 mm.

*Petal shape.*—Obovate.

*Sepal color.*—Green with dark-red veins.

*Color (lower side of petal).*—RHS 40A, HCC 717.

C. Bud:

*Shape.*—Asymmetric.

*Color.*—Same as corolla.

*Pedicel.*—Dark red.

D. Reproductive organs:

*Androecium.*—7–9 anthers.

*Gynoecium.*—4–5 stigma.

E. Spring flowering:

*Response period.*—In Wateringen, The Netherlands in 1988, 80% of plants with at least 1 flower opened 13 weeks after planting unrooted cuttings.

F. Outdoor flower production: The flower count in 1989 in Wateringen, The Netherlands was between 36–41 flowers per plant from June through October observation period.

G. Durability: 80% shatter resistance.

PLANT

A. Foliage:

Form.—Generally kidney-shaped, with open base (see sheet 2).

*Margin.*—Bicrenate.

*Color.*—Dark green.

*Zonation.*—Present on the upperside (RHS 137A).

*Tolerance of botrytis.*—Good.

*Length.*—41 mm.

*Diameter.*—75 mm.

B. General appearance and form:

*Internode length.*—40 mm.

*Branching pattern.*—An average of 4 branches per plant.

*Height.*—268 mm.

*Width.*—268 mm.

CHART A

COMPARISON OF MERIHONEY AND OSNA

| | Merihoney | Osna |
|---|---|---|
| Leaf blade conspicuousness of zone on upper side | very weak to weak | medium to strong |
| Inflorescence diameter | medium to large 132 mm | very large 146 mm |

I claim:

1. A new and distinct cultivar of geranium plant named Merihoney, as illustrated and described.

* * * * *

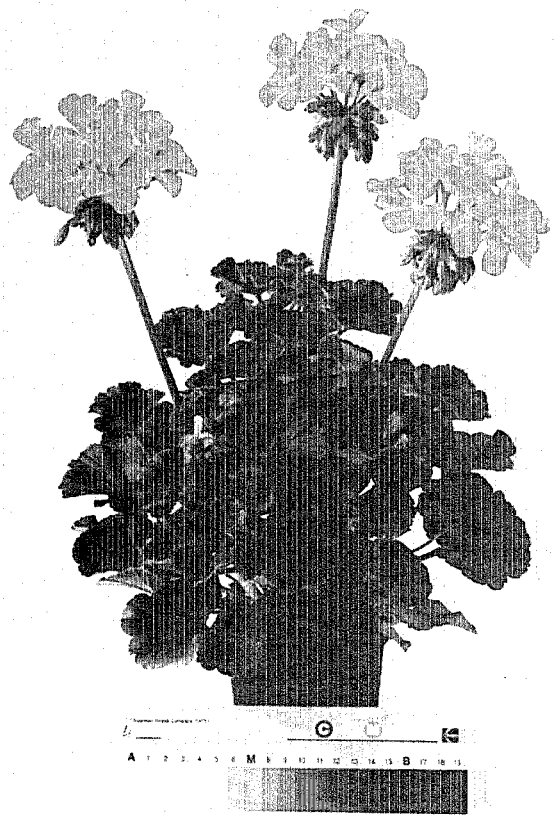

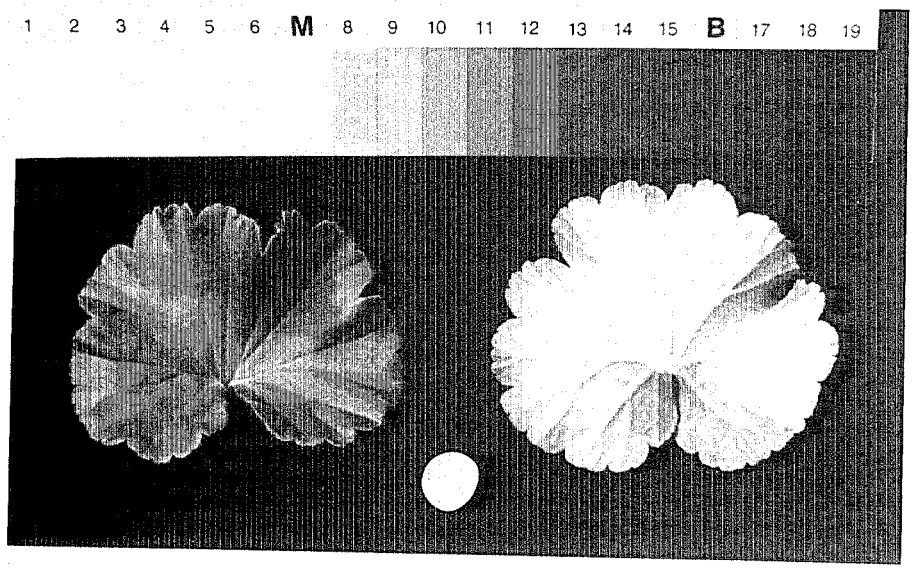
1 2 3 4 5 6 M 8 9 10 11 12 13 14 15 B 17 18 19

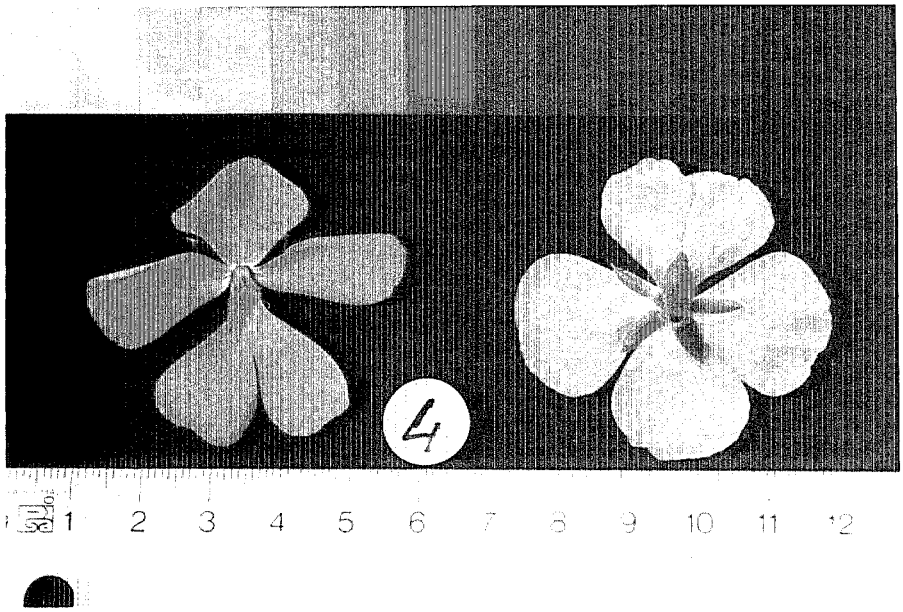
4
1 2 3 4 5 6 7 8 9 10 11 12